US006946543B2

(12) United States Patent
Ward et al.

(10) Patent No.: US 6,946,543 B2
(45) Date of Patent: Sep. 20, 2005

(54) TRUNCATED EGF RECEPTOR (75) Inventors: Colin Wesley Ward, Carlton (AU); Neil Morton McKern, Lilydale (AU); George Oscar Lovrecz, North Balwyn (AU); Robert Nicholas Jorissen, Keysborough (AU); Thomas Peter John Garrett, Brunswick (AU); Thomas Charles Elleman, Westmeadows (AU); Antony Wilkes Burgess, Camberwell (AU); Timothy Edward Adams, Rosanna (AU); Teresa Anne Domagala, Brunswick (AU); Edouard Nice, St. Kilda (AU)

(73) Assignees: Commonwealth Scientific and Industrial Research Organisation, Campbell (AU); Ludwig Institute for Cancer Research, Parkville (AU)

( * ) Notice: Subject to any disclaimer, the term of this patent is extended or adjusted under 35 U.S.C. 154(b) by 0 days.

(21) Appl. No.: 10/070,007

(22) PCT Filed: Jun. 28, 2001

(86) PCT No.: PCT/AU01/00782

§ 371 (c)(1),
(2), (4) Date: Oct. 10, 2002

(87) PCT Pub. No.: WO02/00876

PCT Pub. Date: Jan. 3, 2002

(65) Prior Publication Data

US 2003/0108953 A1 Jun. 12, 2003

(30) Foreign Application Priority Data

Jun. 28, 2000 (AU) .............................. PQ 8418

(51) Int. Cl.[7] .......................... C07K 14/00; C12P 21/06
(52) U.S. Cl. ..................................... 530/350; 435/69.1
(58) Field of Search .......................... 530/350; 435/69.1

(56) References Cited

U.S. PATENT DOCUMENTS

| | | |
|---|---|---|
| 5,218,090 A | 6/1993 | Connors ..................... 530/350 |
| 5,708,156 A | 1/1998 | Ilekis ........................ 536/23.5 |
| 2002/0002276 A1 | 1/2002 | Fitzpatrick et al. | |

FOREIGN PATENT DOCUMENTS

| | | | |
|---|---|---|---|
| WO | 91/03489 | 3/1991 | ............ C07K/7/08 |
| WO | 99/62955 | 9/1999 | ......... C07K/14/705 |

OTHER PUBLICATIONS

Maihle et al. Proc. Nat. Acad. Sci. 1991, vol.88, pp. 1825–1829.*
Ashkenazi et al. Current Opinion in Immunology 1997, vol. 9, pp. 195–200.*
Bishayee, S. (Oct. 2000) "Role of Conformational alteration in the epidermal growth factor receptor (EGFR) function" *Biochemical Pharmacology* 60:1217–1223.
Ekstrand et al. (1992) "Amplified and rearranged epidermal growth factor receptor genes in human glioblastomas reveal deletions of sequences encoding portions of the N– and/or C–terminal tails" *Proc. Natl. Acad. Sci.* USA 89:4309–4313.
Kohda et al. (Jan. 1993) "A 40–kDa Epidermal Growth Factor/Transforming Growth Factor α–binding Domain Produced by Limited Proteolysis of the Extracellular Domain of the Epidermal Growth Factor Receptor" *The Journal of Biological Chemistry* 268(3):1976–1981.
Reiter et al. (1996) "A 1.8kb alternative transcript from the human epidermal growth factor receptor gene encodes a truncated form of the receptor" *Nucleic Acids Research* 24 4050–4056.
Reiter et al. (Jan. 2001) "Comparative genomic sequence analysis and isolation of human and mouse alternative EGFR transcripts encoding truncated receptor isoforms" *Genomics* 71:1–20.
Saxon et al. (Oct. 1999) "Mutagenesis Reveals a Role for Epidermal Growth Factor Receptor Extracellular Subdomain IV in Ligand Binding" *The Journal of Biological Chemistry* 274(40):28356–28362.
Voldborg et al. (1997) "Epidermal growth factor receptor (EGFR) and EGFR mutations, function and possible role in clinical trials" *Annals of Oncology* 8:1197–1206.
Ward et al. (1995) "Insulin and Epidermal Growth Factor Receptors Contain the Csteine Repeat Motif Found in the Tumor Necrosis Factor Receptor" *PROTEINS: Structure, Function and Genetics* 22:141–153.
Elleman, TC et al. (Jul. 2001) "Identification of a Determinant of Epidermal Growth Factor Receptor Ligand–Binding Specificity Using a Truncated, High–Affinity Form of the Ectodomain;" *Biochemistry* 40(30):8930–8939.
Garrett, TPJ et al. (Sep. 2002) "Crystal Structure of a Truncated Epidermal Growth Factor Receptor Extracellular Domain Bound to Transforming Growth Factor;" *Cell* 110(6):763–773.
Jones, J.T. et al. (Mar. 1999) "Binding Specificites and Affinities of egf Domains for ErbB Receptors;" *FEBS Letters* 447:227–231.
Fitzpatrick, V.D. et al. (Jul. 1998) "Formation of a High Affinity Heregulin Binding Site Using the Soluble Extracellular Domains of ErbB2 with ErbB3 or ErbB4;" *FEBS Letters* 431:102–106.

* cited by examiner

*Primary Examiner*—Janet Andres
(74) *Attorney, Agent, or Firm*—Greenlee Winner and Sullivan PC (57) ABSTRACT

The present invention relates to truncated EGF receptor molecules that exhibit increased binding affinities for EGFR ligands such as EGF and TGF-α. The present invention also relates to methods of screening for EGF receptor ligands and methods of treatment which involve the use of these molecules.

23 Claims, 6 Drawing Sheets

TRUNCATED EGF RECEPTOR

CROSS REFERENCE TO RELATED APPLICATIONS

This application is a National Stage Application of PCT International Application No. PCT/AU00/00782, filed on Jun. 28, 2001 which claims priority to Australian Patent Application No. PQ8418, filed on Jun. 28, 2000, both of which are incorporated herein, by reference, in their entirety.

FIELD OF THE INVENTION

The present invention relates to truncated EGF receptor molecules and to pharmaceutical compositions comprising these molecules. The present invention also relates to methods of screening for EGF receptor ligands and methods of treatment which involve the use of these molecules.

BACKGROUND OF THE INVENTION

The epidermal growth factor receptor (EGFR) family consists of four distinct tyrosine kinase receptors, EGFR/HER/ErbB1, HER2/Neu/ErbB2, HER3/ErbB3 and HER4/ErbB4 (1). These receptors are widely expressed in epithelial, mesenchymal and neuronal tissues and play fundamental roles during development and differentiation. They are activated by a family of at least twelve ligands that induce either homo- or hetero-dimerisation of the EGFR homologues. ErbB2 is unable to bind ligand on its own but is a potent co-receptor for all ligands when co-expressed with other members of the EGFR/HER/ErbB family.

The EGFR is a large (1,186 residues), monomeric glycoprotein with a single transmembrane region and a cytoplasmic tyrosine kinase domain flanked by noncatalytic regulatory regions. Sequence analyses have shown that the ectodomain (residues 1–621) contains four sub-domains, here termed L1, CR1, L2 and CR2, where L and CR are acronyms for large and Cys-rich respectively (2, 3). The L1 and L2 domains have also been referred to as domains I and III, respectively (4). The CR domains have been previously referred to as domains II and IV (4), or as S1.1–S1.3 and S2.1–S2.3 where S is an abbreviation for small (2).

Many cancer cells express constitutively active EGFR (5) or other EGFR family members (6). Elevated levels of activated EGFR occur in bladder, breast, lung and brain tumours. Antibodies to EGFR can inhibit ligand activation of EGFR and the growth of many epithelial cell lines. Patients receiving repeated doses of a humanised chimeric anti-EGFR monoclonal antibody (Mab) showed signs of disease stabilization. The large doses required and the cost of production of humanised Mab is likely to limit the application of this type of therapy. These findings indicate that the development of EGF receptor antagonists may be attractive anticancer agents.

SUMMARY OF THE INVENTION

The present inventors have now made the surprising finding that the deletion of residues in the CR2 domain of the EGFR ectodomain gives rise to a truncated ectodomain with enhanced affinity for epidermal growth factors such as (EGF) and/or transforming growth factor-α (TGF-α). This finding goes against recently reported results (8) showing that deletions or mutations in the CR2 region reduce EGFR binding affinity for EGF.

As will be appreciated by those skilled in the art, the truncated EGFR ectodomains of the present invention may provide increased sensitivity in assays which screen for ligands of the EGF receptor. Furthermore, the truncated EGFR ectodomains of the present invention may have therapeutic potential given their high affinity for ligand and their ability to competitively inhibit EGF-induced proliferation responses in vitro.

Accordingly, in a first aspect the present invention provides a truncated EGFR ectodomain, the truncated EGFR ectodomain lacking a substantial portion of the CR2 domain such that the truncated EGFR ectodomain has an increased binding affinity for at least one EGFR ligand when compared to the full length EGFR ectodomain.

The EGFR ligand may be, for example, amphiregulin, heparin binding EGF, β-cellulin, EGF or TGF-α. In a preferred embodiment of the first aspect the truncated EGFR ectodomain has an increased binding affinity for EGF and/or TGF-α.

In a further preferred embodiment of the first aspect the truncated EGFR ectodomain lacks at least the third to seventh modules of the CR2 domain. In a further preferred embodiment, the truncated EGFR ectodomain lacks at least the second to seventh modules of the CR2 domain. The truncated EGFR ectodomain may further lack a portion of the first module of the CR2 domain.

In a further preferred embodiment, the truncated EGFR ectodomain lacks residues 514–621. In yet a further preferred embodiment, the truncated EGFR ectodomain lacks residues 502–621.

Further deletions or mutations may be made to the L1, CR1 and/or L2 sub-domains of the truncated EGFR ectodomain of the present invention, provided that these further deletions or mutations do not substantially affect the binding affinity of the truncated EGFR ectodomain. Preferably, however, the truncated EGFR ectodomain of the present invention comprises the L1, CR1 and L2 subdomains.

In a further preferred embodiment, the truncated EGFR ectodomain comprises residues 1–492 of the EGFR ectodomain. More preferably, the truncated EGFR ectodomain comprises residues 1–501 or residues 1–513 of the EGFR ectodomain.

In a further preferred embodiment, the truncated EGFR ectodomain has an affinity for EGF such that the $K_d$ is less than 30 nM, more preferably less than 25 nM.

In a further preferred embodiment, the truncated EGFR ectodomain has an affinity for TGF-α such that the $K_d$ is less than 45 nM, more preferably less than 40 nM.

In a second aspect the present invention provides a polynucleotide encoding a truncated EGFR ectodomain of the first aspect.

In a third aspect the present invention provides an expression vector comprising a polynucleotide of the second aspect.

In a fourth aspect the present invention provides a host cell comprising an expression vector of the third aspect.

In a fifth aspect, the present invention provides a method for producing a truncated EGFR ectodomain of the first aspect, the method comprising culturing a host cell of the fourth aspect under conditions which allow production of the truncated EGFR ectodomain and isolating the truncated EGFR ectodomain.

In a sixth aspect, the present invention provides a pharmaceutical composition comprising a truncated EGFR ectodomain according to the first aspect and a pharmaceutically acceptable carrier or diluent.

In a seventh aspect, the present invention provides a method of screening a putative compound for the ability to modulate the activity of the EGF receptor, the method comprising exposing the putative compound to a truncated EGFR ectodomain according to the first aspect and monitoring the activity of the truncated EGFR ectodomain.

In the context of the seventh aspect, a suitable assay procedure may involve a competition binding assay in a microplate format, where the putative compound is tested for its ability to inhibit the binding of labelled ligand such as IGF-1 or IGF-2 to the truncated EGF receptor ectodomain. The label may be a radiolabelled tag such as $^{125}$I or a fluorescent tag such as fluorescein isothiocyanate or a lanthanide ion such as europium.

In an eighth aspect the present invention provides a method of treating or preventing a disease associated with signalling by a molecule of the EGF receptor family in a subject, the method comprising administering to the subject a truncated EGFR ectodomain according to the first aspect.

In a preferred embodiment of the eighth aspect, the disease associated with signalling by a molecule of the EGF receptor family is selected from psoriasis and tumour states comprising but not restricted to cancer of the breast, brain, ovary, cervix, pancreas, lung, head and neck, and melanoma, rhabdomyosarcoma, mesothelioma and glioblastoma.

The method of the eighth aspect may be used alone or in combination with other therapeutic measures. For example, the method of the fourth aspect may be used in combination with cytotoxic modalities, such as anti-EGFR antibodies, radiotherapy or chemotherapy, in the treatment of tumour states.

BRIEF DESCRIPTION OF THE FIGURES

FIG. 2: Scatchard analysis of equilibrium binding data. The dissociation constant (KD=1/KA) was calculated from the equilibrium binding response obtained in FIG. 1 by plotting the data in Scatchard format (Req/nC versus Req; see Experimental Procedures). The slope of the linear fit to the data gives KA. (A): sEGFR501 versus hEGF; (B): sEGFR501 versus hTGF-α;. (C): sEGFR621 versus HEGF; (D): sEGFR621 versus hTGFα.

FIG. 3: Inhibition of EGF-stimulated cell mitogenesis by sEGFR501. (A): The stimulation of $^3$H-thymidine incorporation by BaF/3ERX cells using serial dilutions of mEGF. The data was fitted by a sigmoidal function (–) to determine the $EC_{50}$. (B): Inhibition of the mitogenic response of BaF/3ERX cells stimulated with mEGF (207 pM) by: sEGFR501 (■—■), sEGFR621 (●—●) or anti-EGFR antibody Mab528 (▲—▲). Each point was assayed in triplicate. Error bars are shown.

FIG. 4: Covalent cross-linking of sEGFR501 dimers after incubation with mEGF. sEGFR501 (5 μM was incubated with (+) or without (–) mEGF (20 μM in 20 mM HEPES (pH 7.4) containing 150 mM NaCl for 1 h at room temperature followed by the addition of bis(sulfosuccinimidyl)suberate (BS3, Pierce, Rockford, Ill., USA) to a final concentration of 0.5 mM and incubation for a further 30 min. The reaction was terminated and the degree of dimer formation was monitored by SDS-PAGE and immunoblotting with anti-EGFR Mab528 (7) (0.5 μg/ml) and horseradish-peroxidase-labelled goat anti-mouse IgG (Bio-Rad) with detection by ECL (Amersham Pharmacia Biotech). Analysis by non-reducing SDS-PAGE was necessary since the antibody used to detect sEGFR501 (Mab528) is conformation-dependent.

FIG. 5. Analysis of EGF/sEGFR501 interactions using the analytical ultracentrifuge. (A) Sedimentation equilibrium analysis of EGF, sEGFR501 and a mixture of EGF and sEGFR501. The equilibrium distributions were obtained after centrifugation at 12,000 rpm at 20° C. for 16 h. (□) 20 μM EGF; (○) 10 μM sEGFR501, (Δ) 20 μM EGF+10 μM sEGFR501. The lines of best fit drawn though the data for EGF and sEGER501 are for single species and for molecular weight values of 6,000 and 65,600 respectively. The line drawn through the data for the EGF/sEGER501 mixture is the line of best-fit calculated assuming two species with the molecular weight of the first species fixed at 6,000 and a fitted value of 106,400 for the molecular weight of the second species. Inset: The residual plot for the fit of the EGF/sEGFR501 mixture. (B) Meniscus depletion sedimentation analysis of the stoichiometry of EGF binding to sEGFR501. Solutions containing 5 μM sEGFR501 and different molar ratios of EGF:EGFR were spun for 16 h at 20,000 rpm and 20° C. in the XLA analytical ultracentrifuge. Under these conditions sEGER501 and its complexes with EGF are depleted from the meniscus leaving unbound EGF in the supernatant. Optical density measurements at 280 nm enable the amount of unbound EGF near the meniscus to be estimated. (C) Data obtained for the weight-average molecular weight of the "second" species calculated for mixtures of sEGFR501 (5 μM) and EGF at the concentrations indicated under the conditions of panel A above. The solid line corresponds to a simulated curve based on a KD of 30 nM and a dimerisation constant of 4 μM.

DETAILED DESCRIPTION OF THE INVENTION

When used herein the term "EGFR" is intended to encompass members of the EGF receptor family such as the EGF receptor, ErbB2, ErbB3 and ErbB4. In general, EGF receptor family molecules show similar domain arrangements and share significant sequence identity, preferably at least 40% identity.

When used herein, the phrase "full length EGFR ectodomain" refers to the ectodomain consisting of residues 1–621 of the EGF receptor. The amino acid sequence of the full length ectodomain has been previously described (13). The full length ectodomain contains four sub-domains, referred to as L1, CR1, L2 and CR2, where L and CR are acronyms for large and cys-rich respectively.

The CR2 sub-domain consists of the following seven modules joined by linkers of 2 or 3 amino acid residues and bounded by cysteine residues as follows:
First module: cys residues 482–499
Second module: cys residues 502–511
Third module: cys residues 515–531
Fourth module: cys residues 534–555
Fifth module: cys residues 558–567
Sixth module: cys residues 571–593
Seventh module: cys residues 596–612.

The results presented herein show that deletions in the CR2 region of the EGFR ectodomain unexpectedly increase binding affinity of the ectodomain for EGF and/or TGF-α. In light of this information, a person skilled in the art would be able to readily generate a number of candidate truncated ectodomains and screen these candidates for increased ligand affinity and for therapeutic potential.

For example, truncated ectodomains may be prepared by recombinant DNA technology as described herein or as described previously (8). Alternatively, truncated ectodomains may be prepared by subjecting the full length ectodomain or full length receptor to limited proteolysis as described previously (9).

Binding affinity and inhibitor potency may be measured for candidate truncated ectodomains using biosensor technology.

Truncated EGFR ectodomains of the invention may be in a substantially isolated form. It will be understood that the protein may be mixed with carriers or diluents which will not interfere with the intended purpose of the protein and still be regarded as substantially isolated. A truncated ectodomain of the invention may also be in a substantially purified form, in which case it will generally comprise the protein in a preparation in which more than 90%, e.g. 95%, 98% or 99% of the protein in the preparation is a protein of the invention.

In the context of the present invention, the amino acid sequence of the truncated EGFR ectodomain may be modified provided that the modification does not adversely affect the binding affinity of the truncated ectodomain for at least one EGFR ligand. For example, modified ectodomains may be constructed by making various substitutions of residues or sequences or deleting terminal or internal residues or sequences not needed for binding activity. Generally, substitutions should be made conservatively; i.e., the most preferred substitute amino acids are those having physiochemical characteristics resembling those of the residue to be replaced. Similarly, when a deletion or insertion strategy is adopted, the potential effect of the deletion or insertion on biological activity should be considered. In order to preserve the biological activity of the truncated ectodomains, deletions and substitutions will preferably result in homologous or conservatively substituted sequences, meaning that a given residue is replaced by a biologically similar residue. Examples of conservative substitutions include substitution of one aliphatic residue for another, such as Ile, Val, Leu, Met or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known. Moreover, particular amino acid differences between human, murine and other mammalian EGFRs is suggestive of additional conservative substitutions that may be made without altering the essential biological characteristics of the truncated EGFR ectodomains.

Modifications encompassed by the present invention also include various structural forms of the primary protein which retain binding affinities. Due to the presence of ionizable amino and carboxyl groups, for example, a truncated ectodomain may be in the form of acidic or basic salts, or may be in neutral form. Individual amino acid residues may also be modified by oxidation or reduction.

The primary amino acid structure may be modified by forming covalent or aggregative conjugates with other chemical moieties, such as glycosyl groups, lipids, phosphate, acetyl groups and the like, or by creating amino acid sequence mutants. Other modifications within the scope of this invention include covalent or aggregative conjugates of the truncated ectodomain with other proteins or polypeptides, such as by synthesis in recombinant culture as N-terminal or C-terminal fusions. For example, the conjugated polypeptide may be a signal (or leader) polypeptide sequence at the N-terminal region of the protein which co-translationally or post-translationally directs transfer of the protein from its site of synthesis to its site of function inside or outside of the cell membrane or wall (e.g., the yeast α-factor leader). Truncated EGFR ectodomain fusions may comprise peptides added to facilitate purification or identification of the truncated ectodomain (e.g., poly-His) or to enhance stability or delivery of the ectodomain in vivo.

The truncated EGFR ectodomains of the present invention may also be fused to the constant domain of an immunoglobulin molecule. For example, a recombinant chimeric antibody molecule may be produced having truncated EGFR ectodomain sequences substituted for the variable domains of either or both of the immunoglobulin molecule heavy and light chains and having unmodified constant region domains. This may result in a single chimeric antibody molecule having truncated EGFR ectodomains displayed bivalently. Such polyvalent forms of the truncated EGFR ectodomain may have enhanced binding affinity for EGFR ligands. Details relating to the construction of such chimeric antibody molecules are disclosed in WO 89/09622 and EP 315062.

As TGFα exists as a membrane bound form, the truncated ectodomains of the present invention may be used to target compounds to cancer cells. Accordingly, truncated EGFR ectodomain fusions may comprise compounds useful in the diagnosis or treatment of cancer cells such as drugs, isotopes or toxins.

Truncated EGFR ectodomain derivatives may also be obtained by cross-linking agents, such as M-maleimidobenzoyl succinimide ester and N-hydroxysuccinimide, at cysteine and lysine residues. The truncated ectodomains may also be covalently bound through reactive side groups to various insoluble substrates, such as cyanogen bromide-activated, bisoxirane-activated, carbonyldiimidazole-activated or tosyl-activated agarose structures, or by adsorbing to polyolefin surfaces (with or without glutaraldehyde cross-linking). Once bound to a substrate, the truncated ectodomain may be used to selectively bind (for purpose of assay or purification) anti-EGFR antibodies or EGF.

It may also be desirable to use derivatives of the ectodomains of the invention that are conformationally constrained. Conformational constraint refers to the stability and preferred conformation of the three-dimensional shape assumed by a peptide. Conformational constraints include local constraints, involving restricting the conformational mobility of a single residue in a peptide; regional constraints, involving restricting the conformational mobility of a group of residues, which residues may form some secondary structural unit; and global constraints, involving the entire peptide structure.

It will be appreciated that the truncated EGFR ectodomains of the present invention may be used as immunogens, reagents in receptor-based immunoassays, or as binding agents for affinity purification procedures of EGF or other binding ligands.

Truncated EGFR ectodomains may be tested for their ability to modulate receptor activity using a cell-based assay incorporating a stably transfected, EGF-responsive reporter gene (10). The assay addresses the ability of EGF to activate the reporter gene in the presence of novel ligands.

It offers a rapid (results within 6–8 hours of hormone exposure), high-throughput (assay can be conducted in a 96-well format for automated counting) analysis using an extremely sensitive detection system (chemiluminescence). Once candidate compounds have been identified, their ability to antagonise signal transduction via the EGF-R can be assessed using a number of routine in vitro cellular assays such as inhibition of EGF-mediated cell proliferation. Ultimately, the efficiency of truncated EGFR ectodomains as tumour therapeutics may be tested in vitro in animals bearing tumour isografts and xenografts as described (11, 12).

Truncated EGFR ectodomains of the invention (and substances identified by the assay methods of the invention) may preferably be combined with various components to produce compositions of the invention. Preferably the compositions are combined with a pharmaceutically acceptable carrier or diluent to produce a pharmaceutical composition (which may be for human or animal use). Suitable carriers and diluents include isotonic saline solutions, for example phosphate-buffered saline. The compositions may be formulated, for example, for parenteral, intramuscular, intravenous, subcutaneous, intraocular, oral or transdermal administration. Typically, each protein may be administered at a dose of from 0.01 to 30 mg/kg body weight, preferably from 0.1 to 10 mg/kg, more preferably from 0.1 to 1 mg/kg body weight.

The routes of administration and dosages described are intended only as a guide since a skilled practitioner will be able to determine readily the optimum route of administration and dosage for any particular patient and condition.

In view of the ability of the truncated EGFR ectodomains of the present invention to bind strongly to EGFR ligands, the truncated ectodomains will be useful in diagnostic assays for EGFR ligands, as well as in raising antibodies to the EGFR for use in diagnosis and therapy. In addition, purified truncated EGFR ectodomains may be used directly in therapy to bind or scavenge EGFR ligands, thereby providing means for regulating the activities of these ligands. In particular, truncated EGFR ectodomains of the present invention may be administered for the purpose of inhibiting EGF-dependent responses.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

EXPERIMENTAL DETAILS

Materials and Methods

Construction of plasmids used for the expression of truncated forms of hEGFR ectodomain. The plasmid pEGFR, used in the construction of truncated hEGFR cDNAs, comprises nucleotides 167–3970 of hEGFR (13) in the multiple cloning site of plasmid pUC18. Coding is in the opposite sense to the LacZ α peptide, and the insertion is downstream of the XbaI site of pUC18. This plasmid was used later in excision of the truncated constructs for insertion into the mammalian expression vector pEE14 (14).

Construction of pEGFR476. An initial plasmid containing nucleotides 167–3150 of HEGFR was constructed by ligation of a XbaI/NsiI fragment from pEGFR and XbaI/PstI-cut pBluescript KS+. From this plasmid, a 4 kbp fragment BbsI/BgIII fragment (containing all of pBluescript KS+ and nucleotides 167–1150 and 2951–3150 of EGFR) and a 528 bp BbsI/PvuII fragment (nucleotides 1151–1679) were ligated with a 70 bp PCR-derived PvuII and BgIII fragment, encoding amino acids 474–476 of hEGFR, an enterokinase cleavage site and a c-myc epitope tag to facilitate purification. The 70 bp PCR cassette was produced using a similar previous construct (15) as template. A plasmid for mammalian cell transfection, pEGFR476, was constructed from this plasmid by ligation of a 1.6 kbp XbaI/EcoRV fragment 5 with XbaI/SmaI-cut pEE14.

Construction of pEGFR501 and pEGFR513. In each construction PCR was used with three oligonucleotides to produce a fragment of hEGFR cDNA (nucleotides 1121 to 1760 or 1121 to 1797 respectively), followed by a sequence encoding an enterokinase cleavage site, a c-myc epitope tag and a termination codon. The upstream primer in PCR corresponded to an arbitrary choice of nucleotides 1121–1140 of hEGFR cDNA, while two overlapping downstream primers were used to construct additional sequence adjacent to nucleotide 1760 or 1797 respectively. The PCR products were cloned using the pCR-Script vector (Stratagene). In each case this allowed an ApaI fragment harbouring the newly constructed sequence beginning at nucleotide 1738 of hEGFR, to be excised for subsequent insertion into the large ApaI fragment of pEGER (which included the entire pUG18 sequence with hEGFR cDNA to nucleotide 1737), in order to prepare a plasmid encoding a truncated hEGFR with XbaI restriction sites adjacent to the coding sequence. From these pUC18-based plasmids the fragments harbouring the truncated hEGFR cDNAs were excised by XbaI digestion, and inserted into plasmid pEE14 at the XbaI site to prepare plasmids pEGFR501 and pEGFR513 respectively for mammalian cell transfection.

Mutagenesis. The 1.7 kbp fragment harbouring the truncated hEGFR cDNA of pEGFR501 was introduced into M13 mp18 (16) for mutagenesis. Oligonucleotide-directed in vitro mutagenesis, using the USB-T7 GenTM in vitro mutagenesis kit, was employed to produce three single site mutants of the truncated human sEGFR501 ectodomain, with residues Glu367, Gly441 and Glu472 respectively mutated to Lys to match the corresponding residues in chicken EGFR (4). Clones incorporating the mutations were identified by colony hybridisation (17) using $^{32}$P-labelled mutagenic oligonucleotide as a probe, and the mutations were confirmed by DNA sequence analysis (18). Vehicles for mammalian cell expression were generated for each mutant by excising the 1.7 kbp fragment harbouring the mutated sEGFR501 cDNA from M13 RF-DNA by XbaI digestion and inserting it into plasmid pEE14 (16) at the XbaI site.

Cell Culture, DNA Transfection and Protein Analysis. For transient transfection assays, human 293T fibroblasts maintained in DMEM plus 10% fetal calf serum (FCS) were transfected with plasmid DNA using FuGENE (Roche Molecular Biochemicals, Sydney, NSW) according to the manufacturer's instructions. Supernatants were harvested 48 h after transfection, and cell lysates were prepared in NP-40 lysis buffer. To characterise secreted EGFR mutants, aliquots of supernatant and lysate were immunoprecipitated with a monoclonal antibody (9E10) to the c-myc tag, or with Mab 225 (HB-8508, American Type Culture Collection), a conformationally dependent monoclonal antibody recognising the extracellular domain of the hEGFR (19). Immune complexes were collected on Protein A-Sepharose beads (Zymed Laboratories, Bioscientific Pty. Ltd., Gymea, NSW), fractionated by SDS polyacrylamide gel electrophoresis (10% gel) and transferred to nitrocellulose membranes. Truncated hEGFR ectodomains and mutants were identified by probing membranes with horseradish peroxidase (HRP)-conjugated Mab9E10 (Roche), followed by chemilumiscent detection with Pierce Super Signal substrate.

Stable cell lines expressing sEGFR501 were established in the Lec8 mutant cell line from CHOK (7) using glutamine synthetase as a selectable marker (15). Supernatants from methionine sulfoximine (MSX)-resistant cell colonies were screened for secreted receptor by biosensor analysis (see below) or by dot blotting onto nitrocellulose and probing with HRP-Mab9E10. A single cell line was selected for cloning by limiting dilution.

Lec8 cells expressing sEGFR501 protein were cultured in a Celligen Plus bioreactor (New Brunswick Scientific, New Jersey, USA) using 70 g Fibra-Cell Disks carriers with 1.7 L working volume. Continuous perfusion culture using glutamine-free DMEM/F12 medium supplemented with non-essential amino acids, nucleosides and 10% FCS was maintained for 6 weeks. Selection pressure was maintained with 25 $\mu$M MSX for the duration of the fermentation. Perfusion rate was adjusted as required to ensure a residual glucose level of 1.0–1.5 g/L, with a corresponding lactate concentration of 2.0–2.3 $\mu$L.

Purification of Truncated EGFR Ectodomains. For biosensor and AUC analyses, conditioned medium containing the sEGFR truncated proteins (4 L) was adjusted to pH 8.0 with Tris-HCl (Sigma) containing sodium azide (0.02% (w/v)) (TBSA), and particulates removed by centrifugation prior to recovery of c-myc-tagged protein by affinity purification at 4° C. on a column of monoclonal antibody 9E10 covalently-bound to agarose, using peptide elution (15). Eluted protein was further purified by size exclusion chromatography on Superdex 200 (HR10/30, Amersham Pharmacia Biotech) at room temperature using TBSA buffer at a flow rate of 0.8 ml/min. Protein was detected by absorbance at 280 nm.

BIAcore BindingAssays. Protein-protein interactions were monitored in real time on an instrumental optical biosensor using surface plasmon resonance detection (BIAcore 2000 or 3000, BIAcore, Uppsala, Sweden). Recombinant hEGF or hTGF-$\alpha$ (Gropep, Adelaide, Australia) were purified immediately prior to immobilisation by micropreparative RP-HPLC using a SMART system (Amersham Pharmacia Biotech) as described previously (20). The proteins were immobilised onto the biosensor surface using amine coupling chemistry (N-hydroxysuccinimide and N-ethyl-N'-dimethylaminopropyl-carbodiimide) at a flow rate of 4 $\mu$l/min. Typically 100–200 RU were immobilised equivalent to 0.1–0.2 ng/mm$^2$ (20). Automated targeting of immobilisation levels was achieved using the BIAcore 3.1 control software (21).

Prior to analysis, sEGFR621 (23), sEGFR501 and the sEGFR501 mutant samples were characterised by micropreparative size exclusion chromatography (Superose 123.2/30, Amersham Pharmacia Biotech) to ensure size homogeneity (20) and pooled fractions were diluted in BIAcore buffer (HBS: 10 mM Hepes pH 7.4 containing 3.4 mM EDTA, 0.15 mM NaCl and 0.005% (v/v) Tween 20) to the appropriate concentration. Typically, samples (30 $\mu$l) at concentrations of 10–1000 nM were injected sequentially over the sensor surfaces at a flow rate of 5 or 10 $\mu$l/min. Following completion of the injection phase, dissociation was monitored in BIAcore buffer at the same flow rate. The sensor surface and sample blocks were maintained at 25° C. Bound receptor was eluted, and the surface regenerated between injections, using 40 $\mu$l of 10 mM HCl. This treatment did not denature hEGF or hTGF-$\alpha$ immobilised onto the sensor surface, as shown by equivalent signals on re-injection of receptor.

Kinetic rate constants ($k_a$, $k_d$) were determined using the BIAevaluation 3.02 software (BIAcore, http//www.biacore.com/products/eval3.html) as described previously (22), or by global analysis using CLAMP (23, 24). Equilibrium binding constants ($K_A$, $K_D$) were determined by direct non-linear least squares analysis of the binding data using an equation defining steady state equilibrium ($K_A$*Conc*Rmax/($K_A$*Conc*n); BIAevaluation 3.1). The data was also plotted in Scatchard format (Req/nC versus Req, where Req is the biosensor response at equilibrium, n is the valency and C is the concentration) (25).

Analytical Ultracentrifugation. Experiments were performed using a Beckman XL-A analytical ultracentrifuge (Beckman Coulter, Inc., Fullerton, Calif.) equipped with absorption optics, using an An60-Ti rotor with cells containing quartz windows, as described previously (23). Centrifugation experiments were conducted at 20° C. using a sample volume of 100 $\mu$l. Equilibrium sedimentation distributions obtained at 12,000 and 20,000 rpm, were monitored at 280 or 290 nm and analysed using the program SEDEQ1B (26). The partial specific volume of EGF was taken as 0.71 ml/g (23).

Chemical Cross Linking. Chemically cross-linked sEGFR501 dimers were generated by the incubation of sEGFR501 (5 $\mu$m) with mEGF (20 $\mu$M in 20 mM HEPES pH7.4 containing 150 mM NaCl for 1 h at room temperature followed by the addition of bis(sulfosuccinimidyl)suberate (BS3, Pierce, Rockford, Ill., USA) to a final concentration of 0.5 mM and incubation for a further 30 min. The reaction was terminated by the addition of Tris-HCl buffer (pH 7.5) to a final concentration of 10 mM. Monomer-dimer separation was achieved on Novex non-reducing SDS-PAGE gels (10%). Proteins were transferred onto poly(vinyl difluoride) (PVDF) membranes (Bio-Rad, Hercules, Calif., USA) and identified by incubation with anti-EGFR Mab528 (19) (0.5 $\mu$g/ml) followed by horseradish-peroxidase labelled goat anti-mouse IgG (Bio-Rad) and ECL detection (Amersham Pharmacia Biotech).

Cell Proliferation Assays. BaF/3ERX cells, a cell line derived from BaF/3 cells transfected with human EGFR (obtained from Ludwig Institute for Cancer Research, Melbourne) were washed three times to remove residual IL-3 and resuspended in RPMI 1640+10% FCS. Cells were seeded into 96 well plates using a Biomek 2000 robotic autosampler (Beckman) at 2×10$^4$ cells per 200 $\mu$l and incubated for 4 h at 37° C. in 10% CO$_2$. Appropriate concentrations of sEGFR501 or sEGFR621 or the anti-EGFR monoclonal antibody Mab528, were added to the first titration point and titrated in two-fold dilutions across the 96 well plate in duplicate with or without a constant amount of mEGF (207 pM). 3H-Thymidine (0.5 µCi/well) was added and the plates were incubated for 20 h at 37° C. in 5% $CO_2$. The cells were then lysed in 0.5 M NaOH at room temperature for 30 min before harvesting onto nitrocellulose filter mats using an automatic harvester (Tomtec, Conn., USA). The mats were dried in a microwave, placed in a plastic counting bag and scintillant (10 ml) was added. $^3$H-Thymidine incorporation was determined using an automated beta counter (1205 Betaplate, Wallac, Finland).

EXAMPLE 1

Production and Purification of Truncated EGFR Ectodomains

Preliminary analysis of conditioned media from cells transiently expressing sEGFR476, sEGFR501 and sEGFR513 showed that only the latter two truncated receptors gave detectable binding to hEGF immobilised on the BIAcore biosensor (data not shown). Stably transfected Lec8 cells expressing sEGFR501, were generated and used to produce truncated receptor protein at a yield of ~1.8 mg/L of fermentation medium for physical-chemical characterisation.

sEGFR501 purified from a Mab9E10 anti-c-myc peptide affinity column using peptide elution showed a single symmetrical peak on size exclusion chromatography (apparent molecular mass of ~80 kDa) and migrated as a single band of ~70 kDa on SDS-PAGE under reducing conditions (not shown). sEGFR501 gave a unique expected sequence, LEEKKVXQGT (13) on N-terminal amino acid sequence analysis, the X at cycle 7 being due to the presence of a disulphide-bonded cysteine residue at that position. The apparent molecular mass of approximately 70 kDa on SDS-PAGE is due to the residual glycosylation reported for the glycosylation defective Lec 8 cells (33) since the calculated mass of human sEGFR501 apo-protein is ~57.5 kDa. There are eight potential N-linked glycosylation sites in sEGFR501 (13) and incubation of sEGER501 with peptide-N-glycosidase (PNG'ase) at 37° C. resulted in the generation of a major band migrating on SDS-PAGE with an apparent molecular mass of 57–58 kDa (data not shown). We have shown previously using BIAcore analysis that removal of carbohydrate using PNGase does not affect binding of sEGFR621 to the immobilised ligand, in agreement with the concept that glycosylation is required for correct processing but not for biological activity. All subsequent experiments were carried out using the ~70 kDa sEGFR501.

EXAMPLE 2

Affinity Binding of sEGFR501

The BIAcore biosensor was used to determine both the rate and equilibrium binding constants for the interaction between sEGFR501 and hEGF or hTGF-α. Full length ectodomain (sEGFR621) was used as a positive control for the surface reactivity, since this interaction has been studied in detail previously (23, 27).

Figure 1:
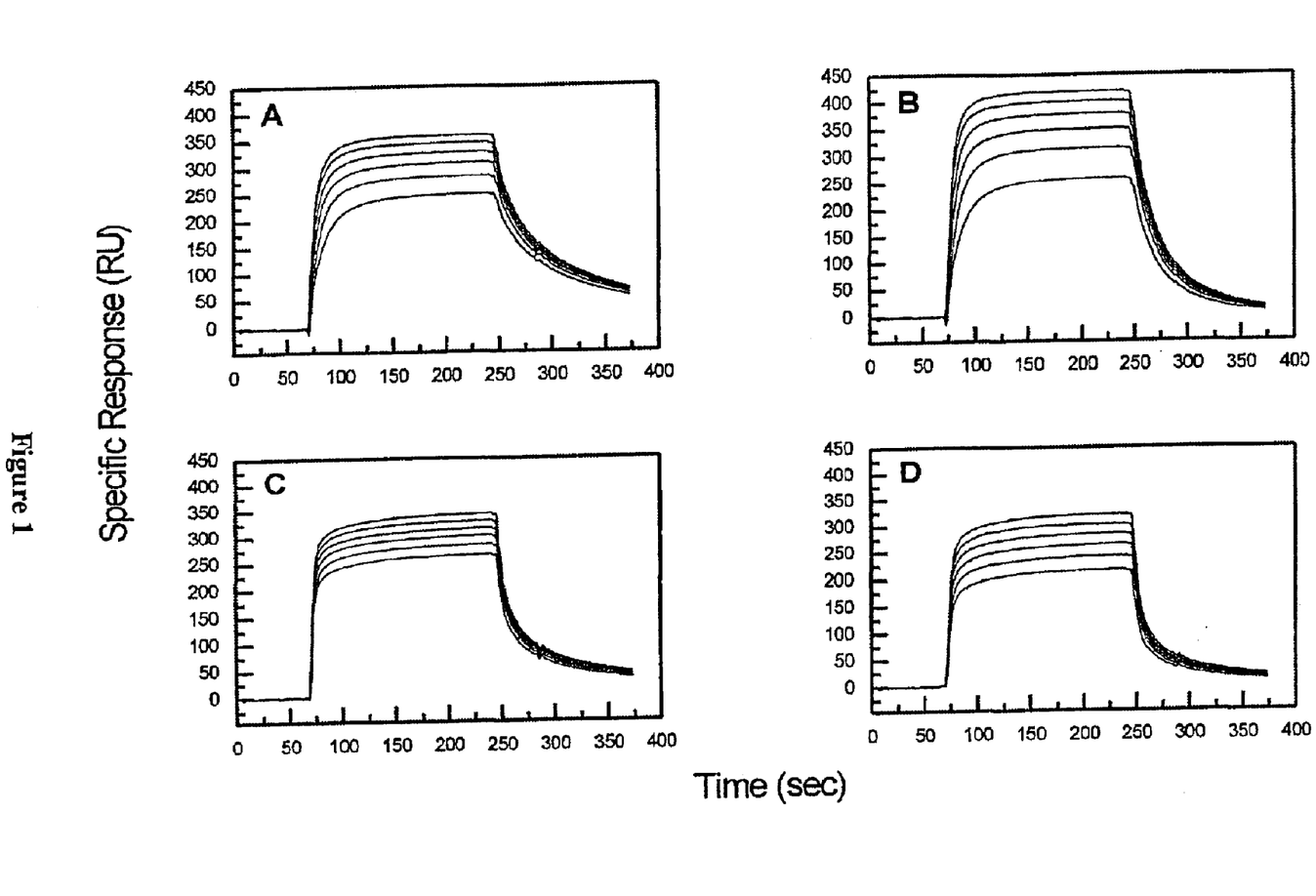
FIG. 1: BIAcore analysis of the interactions between sEGFR501 and sEGFR621 with immobilised hEGF or hTGF-α. (A): sEGFR501 (140, 120, 100, 80, 60 and 40 nM) was passed over immobilised hEGF (160 RU immobilised). Samples (30 μl) were injected at a flow rate of 10 μl/min. (B): sEGFR501 was passed over immobilised hTGF-α (132 RU immobilised). Experimental details were as in panel A. (C): sEGFR621 (1000, 900, 800, 700, 600 and 500 nM) was passed over immobilised HEGF. (D): EGFR621 (concentrations as for panel C) was passed over immobilised hTGF-α. The operating temperature was 25° C. At the end of the injection phase, dissociation was monitored with buffer alone flowing over the sensor surface. The surface was regenerated between samples using 10 mM HCl. The signal obtained when the sample was passed over a parallel blank channel has been subtracted electronically to give the specific response.
Figure 2:
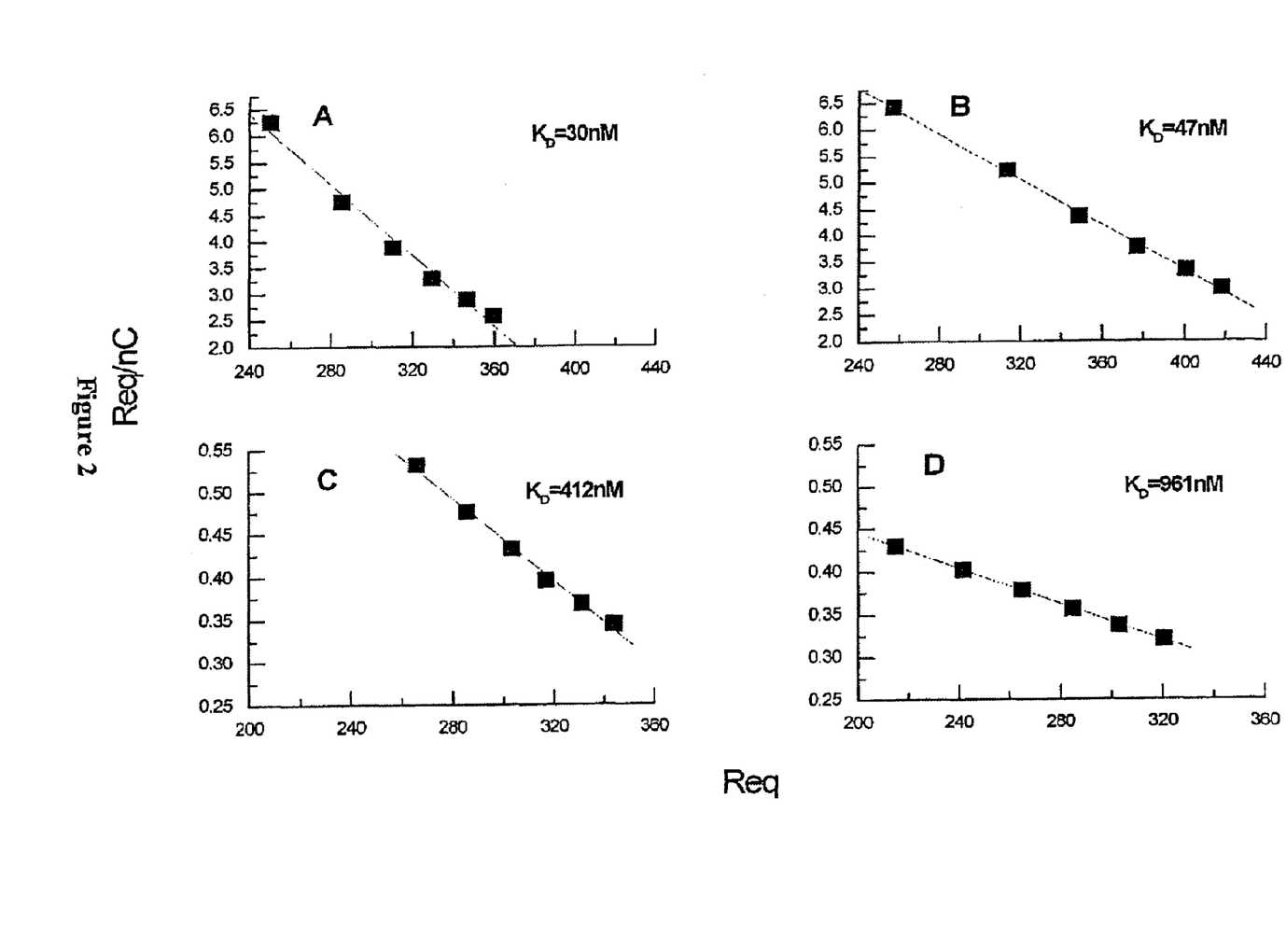

Representative sensorgrams for the interaction between sEGFR501 or sEGFR621 and hEGF or TGF-α are shown in FIG. 1. Visual inspection revealed that the curves approached equilibrium over the concentration ranges tested. Additionally, the hTGF-α sensorgrams appeared to show more rapid, and virtually complete, dissociation. Thermodynamic analysis of the equilibrium binding data in Scatchard format (FIG. 2) indicated KD values of 30 and 47 nM (correlation coefficient R=0.993 and 0.999 respectively) for the interactions between sEGFR501 and immobilised hEGF or hTGF-α and 412 and 961 nM (R=0.997 and 0.999 respectively) for the corresponding interactions with sEGFR621. The values obtained by Scatchard transformation were also confirmed by direct non-linear least squares analysis of the binding data (data not shown) using an equation defining steady state equilibrium (KA*Conc*Rmax/(KA*Conc*n); BIAevaluation 3.1). Using this analysis, KID values of 32 and 46 nM were calculated for the interaction between sEGFR501 and immobilised hEGF and hTGF-α respectively and 570 and 959 nM for the interaction between full-length ectodomain (sEGFR621) and immobilised hEGF and hTGF-α. The values obtained with sEGFR621 were in good agreement with those reported previously (23), confirming the surface viability.

The individual rate constants were determined from those parts of the curves where first order kinetics appeared to be operative (27, 28), and the corresponding dissociation constants calculated (Table 1). Again, there was good agreement between the KD values calculated in this manner and those obtained from the equilibrium binding data. It is interesting to note that the binding curves obtained with both sEGFR501 and sEGFR621 for hTGF-α appeared to be better fitted to a 1:1 model than the corresponding data for the hEGF surface (as suggested by the virtually complete dissociation).

TABLE 1

Comparative kinetic data for ligand binding by truncated and full-length EGFR ectodomains.

| Interaction | $k_a$ ($M^{-1}s^{-1}$) × $10^{-5}$ | $k_d$ ($s^{-1}$) | $K_D$ (nM) |
|---|---|---|---|
| sEGFR501/EGF | 10–17 | 0.02 | 13–21 |
| sEGFR501/TGF-α | 9.3–10.5 | 0.04 | 35–40 |
| sEGFR621/EGF | 2.9–4.8 | 0.08 | 180–300 |
| sEGFR621/TGF-α | 0.7–1.0 | 0.08 | 840–1320 |

EXAMPLE 3

Antagonist Activity of sEGFR501

Figure 3:
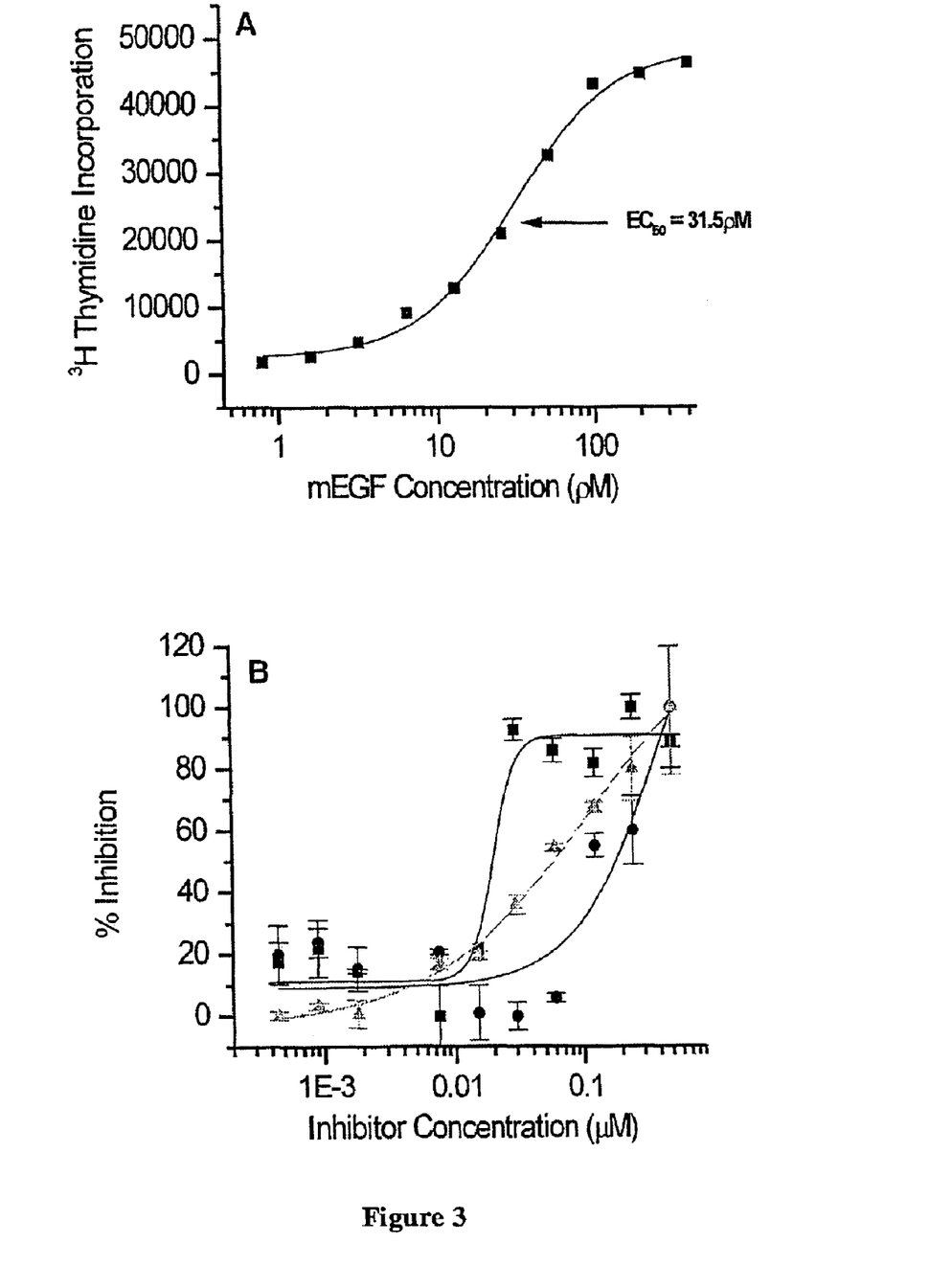

The observation that sEGFR501 bound EGF with high affinity prompted us to test whether sEGFR501 would act as a competitive inhibitor for the mitogenic stimulation of EGFR in a cell-based assay using the BaF/3ERX cell line. This cell line responds to MEGF with an EC50 of approximately 30 pM (FIG. 3A). The competition assay (FIG. 3B) used a constant concentration of mEGF (207 pM), which causes maximal stimulation (FIG. 3A), and varying levels (0.00045–0.5 µM) of sEGFR501, sEGFR621 or the neutralising anti-EGFR monoclonal antibody Mab528 raised against epidermal growth factor receptors on a human epidermoid carcinoma cell line, A431 (19). This antibody has been shown to prevent the growth of A431 cell xenografts, bearing high numbers of EGF receptors, in nude mice. The sEGFR501 (IC50=0.02 µM) was almost 10 fold more potent than the full-length ectodomain (IC50=0.15 µM) and approximately 3-fold more potent than the Mab528 anti-EGFR monoclonal antibody (IC50=0.06 µM).

EXAMPLE 4

Dimerisalion of sEGFR501

Figure 4:
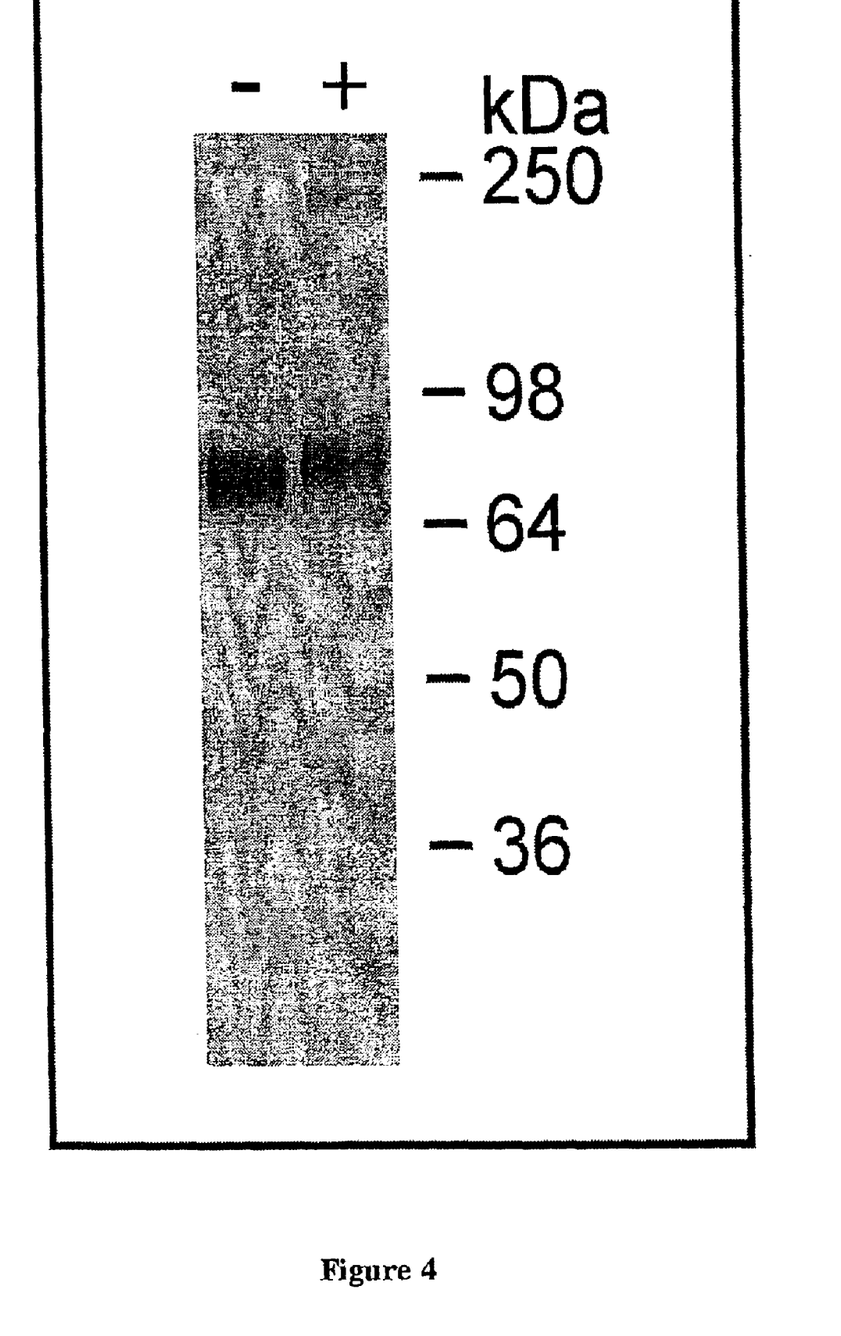

Chemical cross-linking revealed that sEGFR501 formed dimeric complexes in the presence of ligand. In the presence of 20 μM mEGF, a single high molecular weight species (apparent Mr 180,000 Da) was formed after chemical cross-linking which was not detectable when the cross-linking was attempted in the absence of ligand (FIG. 4). Western blotting was employed to confirm the authenticity of the bands observed, but similar data were obtained with silver or Coomassie blue staining. In addition, size exclusion chromatographic analysis of the reaction mixture, using a TSK G2000SW column developed with a mobile phase of PBS at a flow rate of 0.25 ml/min, showed a peak of apparent Mr 158,000 which corresponded to dimer (data not shown). Similar results have previously been obtained with sEGFR621.

Figure 5:
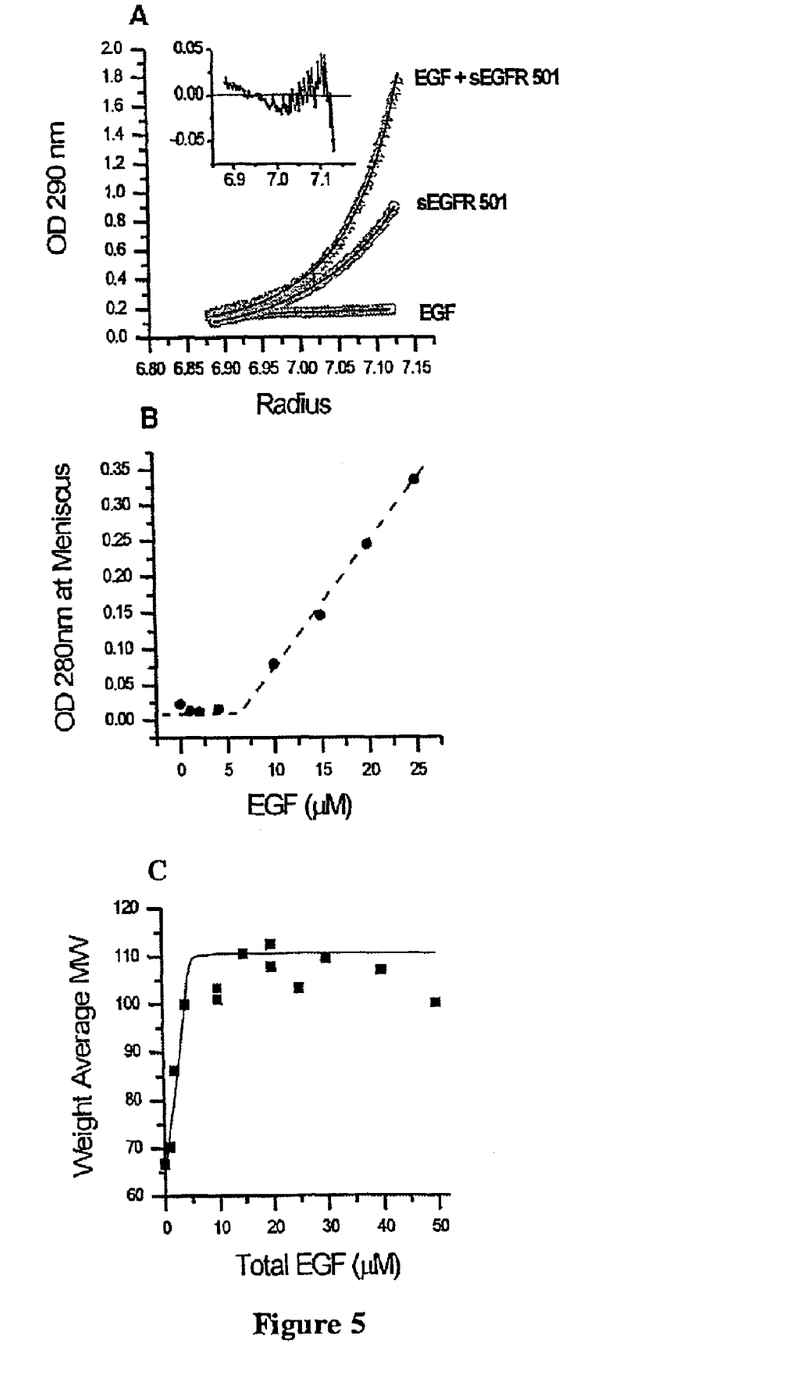

Analytical ultracentrifugation showed that the EGF binding sites on sEGFR501 were saturated at an equimolar ratio of ligand and receptor leading to the formation of a 2:2 EGF/sEGFR501 complex (FIG. 5). The data for 20 μM EGF alone (FIG. 5A) indicate a single solute of molecular weight 5,980 Da, in good agreement with the value calculated from the amino acid composition (6,040 Da). The molecular weight (65,600 Da) and partial specific volume (0.71 ml/g) determined for 10 μM sEGFR501 alone was calculated from the sedimentation equilibrium distribution (FIG. 5A) and is based on the known amino acid composition and a calculated value of 12% (w/w) for the carbohydrate composition.

Sedimentation equilibrium data for a mixture of EGF (20 μM) and sEGFR501 (10 μM) was analyzed assuming two species (FIG. 5A). The molecular weight of the first species was fixed at the value obtained for free EGF (6,000 Da) with the molecular weight and weight fraction of the second species used as fitting parameters. Under these conditions the molecular weight of the second species provides a good approximation to the weight-average molecular weight of sEGFR501 and its complexes. The best-fit value showed a complex of weight-average MW 106,400 Da, higher than predicted for a 1:1 complex (71,600 Da) and more consistent with the formation of a significant proportion of dimeric 2:2 EGF/sEGFR501 complex (see below). High-speed meniscus depletion experiments were performed to determine the molar ratio required for saturation of sEGFR501 with EGF (FIG. 5B). A solution of sEGFR501 (5 μM) was titrated with EGF to determine the molar ratio at which free EGF is detectable at the meniscus. The results show that this occurs above 5 μM EGF, implying an equimolar ratio is required for saturation of the EGF binding site(s) on sEGFR501. These data, taken together with the observed weight average molecular weight of the EGF/sEGFR501 complex obtained from the equilibrium analysis (FIG. 5A), confirm that the stoichiometry of the EGF/sEGFR501 dimeric species is 2:2 not 2:1.

Sedimentation equilibrium was used for the analysis of data obtained for sEGFR501 (5 μM) in the presence of a range of EGF concentrations (FIG. 5C). The weight average molecular weight obtained for the "second" species increases rapidly as the ratio of EGF/sEGFR501 is increased to 1:1 and then tends to plateau around approximately 108,000 at ratios above 2:1 (FIG. 5C). The data in FIG. 5A could also be fitted assuming a mixture of 1:1 and 2:2 complexes with weight fractions of the monomeric and dimeric sEGFR501 complexes of 57% and 31% respectively. Similar data was obtained with sEGFR621 (23).

EXAMPLE 5 sEGFR501-441 Mutant Binding Studies

Biosensor analysis was also used to analyse the binding of the transiently expressed sEGFR501 mutants to both immobilised hEGF and hTGF-α surfaces. The presence of the mutant proteins in culture supernatants from transfected cell lines was demonstrated by both immunoblotting with the anti-EGFR monoclonal antibody, Mab 528, and biosensor analysis using Mab 528 immobilised on the surface. Culture supernatants from all cell lines showed demonstrable binding to the Mab surface (441>472=wt>367) (data not shown).

In preliminary experiments, the Glu367Lys mutant and the Glu472Lys mutant showed similar binding characteristics to sEGFR501 when passed over the hEGF sensor surface (data not shown). The Gly441Lys mutant showed much reduced binding, even though the Mab528 surface had indicated that the Gly441Lys mutant was present at higher concentrations than sEGFR501. Interestingly, when the same samples were passed over the parallel hTGF-α sensor surface the Gly441Lys mutant now showed the highest binding, whilst the binding of the Glu367Lys mutant the Glu472Lys mutant and wild type sEGFR501 were again similar but lower.

Figure 6:
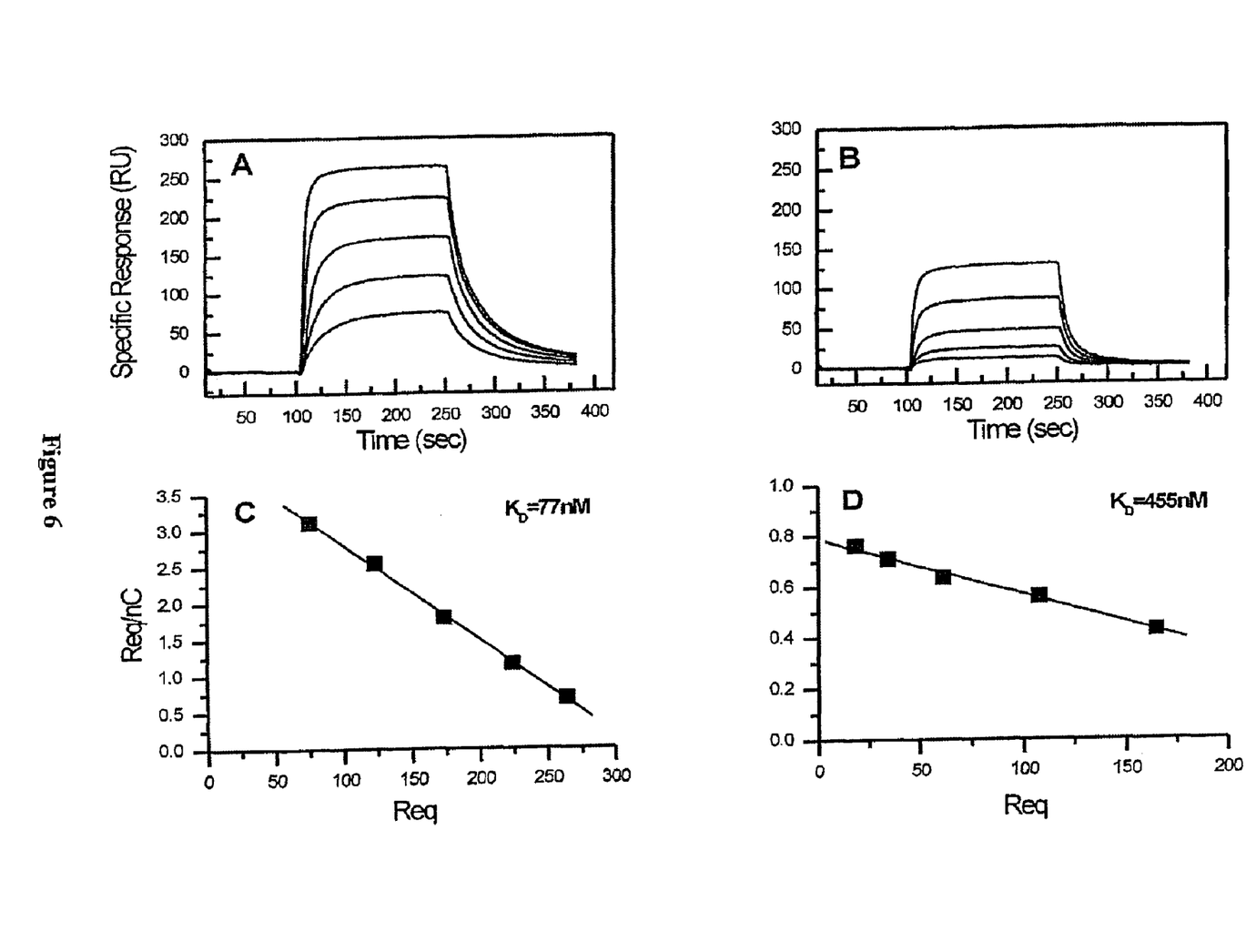
FIG. 6: BIAcore analysis of the binding of the Gly441Lys sEGFR501 mutant to immobilised hEGF and hTGF-α. Purified Gly441LyssEGFR501 (24–385 nM) was passed over immobilised hTGF-α (Panel A) or hEGF (Panel B) using the experimental conditions described in FIG. 1. The corresponding Scatchard analysis, using the equilibrium binding values obtained from these sensorgrams, is shown below (Panels C,D).

For full biosensor analysis the mutant proteins present in the conditioned media from transient transfected 293T fibroblasts were concentrated and purified by a combination of affinity purification using the 9E10 monoclonal antibody and size exclusion chromatography on Superdex 200 and Superose 12. The sensorgrams obtained with the immobilised hEGF and hTGF-α surfaces (160 and 132 RU immobilised respectively) are shown in FIGS. 6A,B. As we had observed in the preliminary experiments, whilst the binding characteristics of the Glu367Lys and Glu472Lys mutants were essentially undistinguishable from those of sEGFR501 shown in FIG. 1 (data not shown) the Gly441Lys mutant again showed preferential binding to the hTGF-α surface (FIGS. 6A,B). Scatchard analysis of the equilibrium binding data (FIGS. 6C,D) indicated that whilst binding to the TGF-α surface was similar to that observed with sEGFR501 (KD=77 nM, correlation coefficient R=0.999), the reactivity of the Gly441Lys mutant towards the EGF surface was now considerably reduced (KD=455 nM, R=0.995). Similar values (78 nM and 469 nM) were obtained by direct non-linear least squares analysis of the binding data (data not shown) using the equation defining steady state equilibrium.

Kinetic analysis of the binding data (Table 2) indicated that the interaction with the immobilised TGF-α could be described by an association rate constant (ka) of 5.2–6.9× 10-5M-1s-1 and a dissociation rate constant (kd) of 0.025s-1 giving a KD=kd/ka of 36–44 nM. The corresponding interaction with EGF was described by a ka of 1.9–2.3× 10-5M-1s-1 and a significantly faster kd of 0.103s-1 giving a KD=kd/ka of 442–545 nM, in good agreement with the results observed from the thermodynamic analysis.

TABLE 2

Kinetic analysis of the binding of Gly$^{441}$Lys sEGFR501 to immobilised hEGF and hTGF-α.

| Interaction | $k_a$ (M$^{-1}$s$^{-1}$) × 10$^{-5}$ | $k_d$ (s$^{-1}$) | $K_D$ (nM) |
|---|---|---|---|
| TGF-α | 5.2–6.9 | 0.025 | 36–48 |
| EGF | 1.9–2.3 | 0.103 | 442–545 |

Discussion

The characteristics of a truncated version of the EGFR ectodomain (sEGFR501) that binds hEGF and hTGF-α with high affinity (Table 1, FIGS. 1 and 2) are described herein. The KD values of 13–21 nM for hEGF binding to sEGFR501 are similar to those, (15–30 nM), seen with chemically cross-linked dimers of full-length EGFR ectodomain and are 10 to 25-fold higher than the values generally reported for soluble, full-length EGFR ectodomain derived from either A431 tumour cells, transfected Sf9 insect cells or CHO cells.

sEGFR501, which lacks most of CR2, exhibits ligand-induced receptor dimerisation (FIGS. 4 and 5) indicating that the regions responsible for dimerisation are unlikely to include CR2. It also confirms that membrane anchoring is not required for the generation of high affinity dimers in contrast to the situation with ErbB2/ErbB3 heterodimers and neuregulin. The ultracentrifugation analyses showed that the binding sites on sEGFR501 were saturated, and the extent of dimerisation began to plateau, at molar ratios greater than of 1:1 (FIG. 5C), even at the relatively low concentration of sEGFR501 of 5 µM (320 µg/ml). This compares favourably with the small angle X-ray scattering data and our previous analytical ultracentrifugation analyses that showed that sEGFR621 dimerisation, induced by EGF or TGF-α binding, reached a maximum when the ratio of EGF/sEGFR was 1:1.

It is envisaged that sEGFR501 will have therapeutic potential given its high affinity for ligand and its ability to competitively inhibit EGF-induced proliferation responses in a model cell system (FIG. 3). This inhibition was greater than that achieved in the same assay with a neutralising monoclonal antibody raised against the receptor (Mab528), chimeric forms of which (C225) are currently in clinical trials.

sEGFR501 was also employed to investigate the residue responsible for the differential binding between hTGF-α and hEGF observed with chicken EGFR (9). These data demonstrate that the Lys442 in chicken EGFR, which corresponds to Gly441 in hEGFR, is the residue responsible for discriminating between hTGF-α and hEGF binding.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are apparent to those skilled in molecular biology or related fields are intended to be within the scope of the invention.

REFERENCES

1. Burgess A W and Thumwood C M. (1994) Pathology 26, 453–463
2. Bajaj, M., Waterfield, M. D., Schlessinger, J., Taylor, W. R. and Blundell, T. (1987) Biochim.Biophys. Acta. 916, 220–226
3. Ward, C. W., Hoyne, P. A. and Flegg, R. H. (1995) Proteins-Struct. Funct. Genet. 22, 141–153
4. Lax, I., Johnson, A., Howk, R., Sap, J., Bellot, F., Winlder, M., Ullrich, A., Vennstrom, B., Schlessinger, J., and Givol, D. (1988) Molec. Cellul. Biol. 8, 1970–1978
5. Sandgreen, E. P., Luettke, N. C., Palmiter, R. D., Brinster, R. L., Lee, D. C. (1990) Cell 61, 1121–1135
6. Hines, N. E. (1993) Semin. Cancer Biol. 4, 19–26
7. Stanley, P. (1989) Molec. Cellul. Biol. 9, 377–383
8. Saxon, M. L. and Lee, D. C. (1999) J. Biol. Chem. 274, 28356–28362
9. Kohda, D., Odaka, M., Lax, I., Kawasaid, H., Suzuid, K., Ullrich, A., Schlessinger, J. and Inagaid, F. (1993) J. Biol. Chem. 268, 1976–1981
10. Souriau, C., Fort, P., Roux, P., Hartley, O., Lefranc, M-P., Weill, M., 1997, Nucleic Acids Res. 25:1585–1590
11. Rockwell, P., O'Connor, W. J., King, K., Goldstein, N. I., Zhang, L. M., Stein, C. A., 1997, Proc Natl Acad Sci USA 94:6523–6528;
12. Prewett, M., Rothman, M., Waksal, H., Feldman, M., Bander, N. H., Hicklin, D. J., 1998 Clin Cancer Res 4:2957–2966
13. Ullrich, A., Coussens, L., Hayflick, J. S., Dull, T. J., Gray, A., Tam, A. W., Lee, J., Yarden, Y., Libermann, T. A., Schlessinger, J., Downard, J., Mayes, E. L. V., Whittle, N., Waterfield, M. D. and Seeburg, P. H. (1984) Nature 309, 418–425
14. Bebbington, C. R. and Hentschel, C. C. G. (1987) in DNA Cloning (Glover, D., ed.), Vol. III, pp. 163–188, IRL Press, Oxford, U.K.
15. McKern, N. M., Lou, M., Frenkel, M. J., Verkuylen, A., Bentley, J. D., Lovrecz, G. O., Ivancic, N., Elleman, T. C., Garrett, T. P. J., Cosgrove L. & Ward, C. W. (1997) Protein Sci. 6, 2663–2666
16. Norrander, J., Kempe, T. and Messing, J. (1983) Gene 26, 101–106
17. Carter, P. (1987) Methods Enzymol. 154, 382–403
18. Sanger, F., Nicklen, S. and Coulson, A. R. (1977) Proc. Natl. Acad. Sci. U.S.A. 74, 5463–5467
19. Gill, G. N., Kawamoto, T., Cochet, C., Le, A., Sato, J. D., Masui, H., McLeod, C., and Mendelsohn, J. (1984) J. Biol. Chem. 259, 7755–7760
20. Nice, E., Lackmann, M., Smyth, F., Fabri, L., Burgess, A. W. (1994) J Chromatogr. A 660, 169–185
21. Catimel B, Domagala T, Nerrie M, Weinstock J, White S, Abud H, Heath J and Nice E, (1999) Prot. Pept Lett. 6, 319–340
22. Catimel, B., Nerrie, M., Lee, F. T., Scott, A. M., Ritter, G., Welt, S., Old, L. J., Burgess, A. W. and and Nice, E. C. (1997) J. Chromatogr. 776, 15–30.
23. Domagala, T., Konstantopoulos, N., Smyth, F., Jorissen, R. N., Fabri, L., Geleick, D., Lax, I., Schlessinger, J., Sawyer, W., Howlett, G. J., Burgess, A. W. and Nice, E. C. (2000) Growth Factors 18, 11–29
24. Morton, T. A. and Myszka, D. G. (1998) Methods Enzymol. 295, 268–294.
25. Hammacher, A., Simpson, R. J. and Nice, E. C. (1996) 271, 5464–5473
26. Minton, A. P. (1994) In Modern Analytical Ultracentrifugation: Acquisition and Interpretation of Data for Biological and Synhtetic Polymer systems, Schuster, T. M. and Laue, T. M. eds, Birkhauser, Boston, p81
27. De Crescenzo, G., Grothe, S., Lortie, R., Debanne, M. T. and O'Connor-McCourt M. (2000) Biochemistry, 9466–9476
28. Nice E. C. and Catimel B. (1999) BioEssays 21, 339–352

What is claimed is:

1. An isolated truncated ErbB1 ectodomain comprising at least residues 1–492 of ErbB1 and lacking at least the third to seventh modules of the ErbB1 CR2 domain such that the truncated ErbB1 ectodomain has an increased binding affinity for at least one ErbB1 ligand when compared to the full length ErbB1 ectodomain.

2. The truncated ErbB1 ectodomain as claimed in claim 1 wherein the truncated ErbB1 ectodomain has an increased binding affinity for EGF and/or TGF-α.

3. The truncated ErbB1 ectodomain as claimed in claim 2 wherein the truncated ErbB1 ectodomain lacks at least the second to seventh modules of the CR2 domain.

4. The truncated ErbB1 ectodomain as claimed in claim 2 wherein the truncated ErbB1 ectodomain further lacks a portion of the first module of the CR2 domain.

5. The truncated ErbB1 ectodomain as claimed in claim 2 wherein the truncated ErbB1 ectodomain lacks residues 514–621.

6. The truncated ErbB1 ectodomain as claimed in claim 2 wherein the truncated ErbB1 ectodomain lacks residues 502–621.

7. The truncated ErbB1 ectodomain as claimed in claim 2 wherein the truncated ErbB1 ectodomain has an affinity for EGF such that the Kd is less than 30 nM.

8. The truncated ErbB1 ectodomain as claimed in claim 2 wherein the truncated ErbB1 ectodomain has an affinity for TGF-α such that the Kd is less than 45 nM.

9. A chimeric or fusion protein comprising a truncated ErbB1 ectodomain as claimed in claim 2.

10. The chimeric or fusion protein as claimed in claim 9 wherein the truncated ErbB1 ectodomain is conjugated to an immunoglobulin constant domain.

11. The truncated ErbB1 ectodomain as claimed in claim 1 wherein the truncated ErbB1 ectodomain lacks at least the second to seventh modules of the CR2 domain.

12. The truncated ErbB1 ectodomain as claimed in claim 1 wherein the truncated ErbB1 ectodomain further lacks a portion of the first module of the CR2 domain.

13. The truncated ErbB1 ectodomain as claimed in claim 1 wherein the truncated ErbB1 ectodomain lacks residues 514–621.

14. The truncated ErbB1 ectodomain as claimed in claim 1 wherein the truncated ErbB1 ectodomain lacks residues 502–621.

15. The truncated ErbB1 ectodomain as claimed in claim 1 wherein the truncated ErbB1 ectodomain has an affinity for EGF such that the Kd is less than 30 nM.

16. The truncated ErbB1 ectodomain as claimed in claim 1 wherein the truncated ErbB1 ectodomain has an affinity for TGF-α such that the Kd is less than 45 nM.

17. A chimeric or fusion protein comprising a truncated ErbB1 ectodomain as claimed in claim 1.

18. The chimeric or fusion protein as claimed in claim 17 wherein the truncated ErbB1 ectodomain is conjugated to an immunoglobulin constant domain.

19. A pharmaceutical composition comprising the chimeric or fusion construct as claimed in claim 17 and a pharmaceutically acceptable carrier or diluent.

20. A pharmaceutical composition comprising the truncated ErbB1 ectodomain as claimed in claim 1 and a pharmaceutically acceptable carrier or diluent.

21. An isolated truncated ErbB1 ectodomain comprising residues 1–501 or residues 1–513 of the ErbB1 ectodomain and lacking at least the third to seventh modules of the ErbB1 CR2 domain such that the truncated ErbB1 ectodomain has an increased binding affinity for at least one ErbB1 ligand when compared to the full length ErbB1 ectodomain.

22. An isolated truncated ErbB1 ectodomain consisting of residues 1–501 or 1–513 of the ErbB1 ectodomain.

23. A dimer of the chimeric or fusion protein of claim 18 or claim 10.

* * * * *

UNITED STATES PATENT AND TRADEMARK OFFICE
CERTIFICATE OF CORRECTION

PATENT NO. : 6,946,543 B2
DATED : September 20, 2005
INVENTOR(S) : Ward et al.

It is certified that error appears in the above-identified patent and that said Letters Patent is hereby corrected as shown below:

Title page,
Item [75], Inventors, delete "Neil Morton McKern" and replace with -- Neil Moreton McKern --.

Column 3,
Lines 42 and 57, delete "HEGF" and replace with -- hEGF --.

Column 8,
Line 13, delete "HEGFR" and replace with -- hEGFR --.
Line 24, delete "5" after "fragment".

Column 10,
Lines 3 and 4, delete "123.2/30" and replace with -- 12 3.2/30 --.

Column 12,
Line 10, delete "KID" and replace with -- KD --.
Line 48, delete "MEGF" and replace with -- mEGF --.

Signed and Sealed this

Fifteenth Day of November, 2005

JON W. DUDAS
*Director of the United States Patent and Trademark Office*